(12) United States Patent
Bark et al.

(10) Patent No.: US 6,919,492 B2
(45) Date of Patent: Jul. 19, 2005

(54) SKIN BARRIER STRIP HAVING TRIANGULAR CROSS SECTION

(75) Inventors: Jeffrey E. Bark, Libertyville, IL (US); Michael A. Metz, Chicago, IL (US)

(73) Assignee: Hollister Incorporated, Libertyville, IL (US)

(*) Notice: Subject to any disclaimer, the term of this patent is extended or adjusted under 35 U.S.C. 154(b) by 394 days.

(21) Appl. No.: 10/158,612

(22) Filed: May 30, 2002

(65) Prior Publication Data

US 2003/0004451 A1 Jan. 2, 2003

Related U.S. Application Data

(60) Provisional application No. 60/297,874, filed on Jun. 13, 2001.

(51) Int. Cl.[7] ............................ A61F 15/00; A61F 5/44; A61F 13/02
(52) U.S. Cl. ........................ 602/56; 604/344; 604/307; 602/58
(58) Field of Search ............................... 604/332–344, 604/277, 307, 327, 352; 602/54–56, 58

(56) References Cited

U.S. PATENT DOCUMENTS

| | | | |
|---|---|---|---|
| 2,221,321 A | | 11/1940 | Foron ........................... 128/283 |
| 3,074,404 A | | 1/1963 | Robinson ..................... 128/283 |
| 4,109,657 A | | 8/1978 | Carrington ................... 128/283 |
| 4,219,023 A | | 8/1980 | Galindo ........................ 128/283 |
| 4,475,908 A | * | 10/1984 | Lloyd ........................... 604/339 |
| 4,551,490 A | | 11/1985 | Doyle et al. .................. 524/22 |
| 4,710,182 A | * | 12/1987 | Bryson ......................... 604/339 |
| 4,723,952 A | | 2/1988 | Esposito ....................... 604/338 |
| 4,867,748 A | * | 9/1989 | Samuelsen ................... 604/336 |
| 4,927,687 A | * | 5/1990 | Nuwayser ..................... 424/449 |
| 4,928,681 A | * | 5/1990 | Langston et al. ............. 602/58 |
| 5,409,472 A | * | 4/1995 | Rawlings et al. ............ 604/307 |
| 5,429,625 A | | 7/1995 | Holmberg ..................... 604/338 |
| 5,730,736 A | | 3/1998 | Sawers et al. ................ 604/344 |
| 5,834,009 A | | 11/1998 | Sawers et al. ................ 424/443 |
| 6,071,268 A | | 6/2000 | Wagner ........................ 604/332 |
| 6,171,289 B1 | | 1/2001 | Millot et al. ................. 604/336 |
| 6,241,712 B1 | * | 6/2001 | Steer ............................ 604/333 |
| 6,332,879 B1 | * | 12/2001 | Nielsen et al. ............... 604/344 |
| 6,362,387 B1 | * | 3/2002 | Carlson et al. ............... 602/41 |
| 6,569,134 B1 | * | 5/2003 | Leise et al. .................. 604/332 |
| 6,570,050 B2 | * | 5/2003 | Augustine et al. ........... 602/41 |
| 6,635,050 B1 | * | 10/2003 | Jensen et al. ................. 606/1 |

FOREIGN PATENT DOCUMENTS

| | | | |
|---|---|---|---|
| EP | 0 410 921 A2 | * 1/1991 | .......... A61M/37/00 |
| EP | 0 686 381 A1 | 12/1995 | |
| EP | 0 756 854 A1 | 2/1997 | |
| EP | 1 053 725 A1 | 11/2000 | |
| GB | 2 022 670 A1 | 12/1979 | |
| WO | WO 99/11302 | 3/1999 | |

* cited by examiner

*Primary Examiner*—Larry I. Schwartz
*Assistant Examiner*—Michael G. Bogart
(74) *Attorney, Agent, or Firm*—Marshall, Gerstein & Borun LLP

(57) ABSTRACT

An elongate rectilinear strip of skin barrier material is disclosed, such strip being of generally uniform triangular cross section through its length, such triangle having at least two, and preferably three, unequal sides. The strip may be cut to desired length and formed, stretched and/or molded by a user into a generally circular shape or into some other shape that extends about and follows the outline of a wound or stoma.

18 Claims, 1 Drawing Sheet

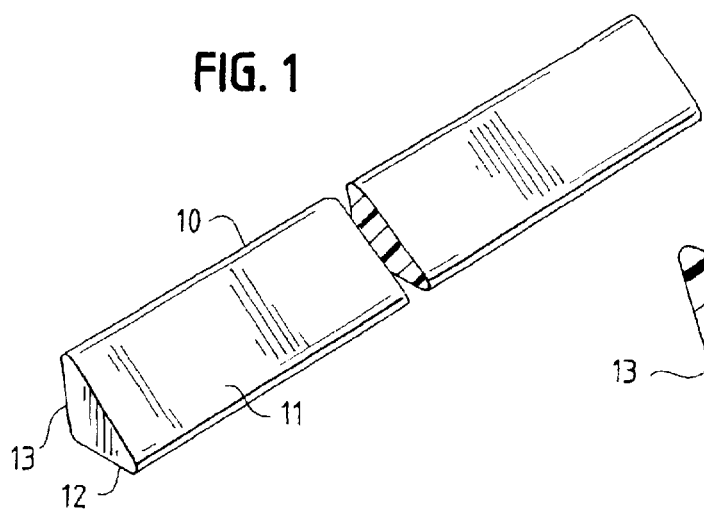
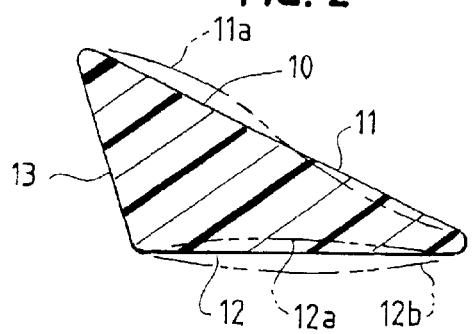
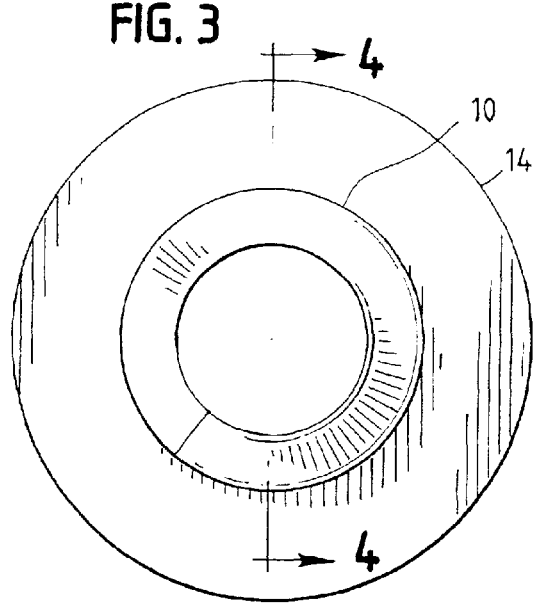
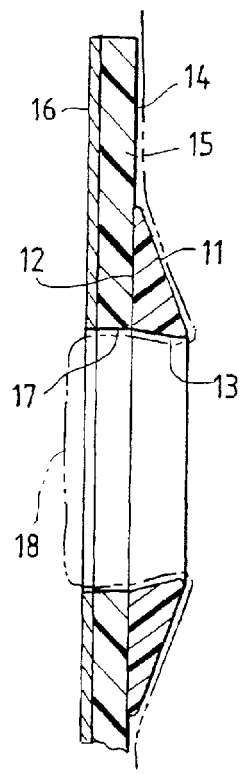
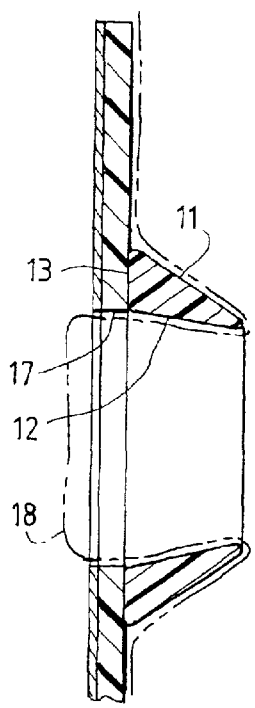
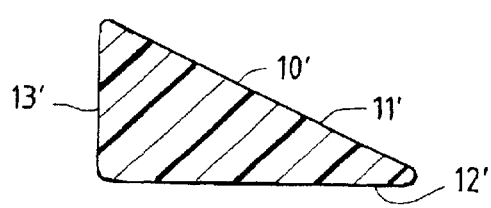
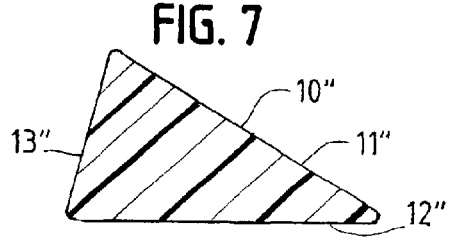

SKIN BARRIER STRIP HAVING TRIANGULAR CROSS SECTION

REFERENCE TO RELATED APPLICATIONS

We claim priority to, and are entitled to the benefit of the filing date of now U.S. Provisional Application No. 60/297,874, filed Jun. 13, 2001, as to all subject matter commonly disclosed therein.

BACKGROUND AND SUMMARY

The term "skin barrier" is widely used in the medical field to refer to any of a variety of sticky, pliant, moisture-absorbing, skinfriendly adhesive compositions commonly utilized in ostomy appliances and wound dressings. Most frequently, such a skin barrier composition constitutes a continuous adhesive phase with particles of one or more liquid-absorbing and swellable hydrocolloids dispersed throughout the adhesive and constituting a discontinuous phase. Such skin barriers are commonly used with ostomy appliances to seal the faceplates of such appliances against peristomal skin surfaces and thereby protect those surfaces from exposure to stomal effluent as well as to prevent leakage of such effluent from about the stoma-receiving openings of the pouches.

The initial tack of a hydrocolloid skin barrier material, usually referred to as "dry tack," is provided by the continuous adhesive phase but, because such a skin barrier material is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. Nos. 5,492,943 and 4,551,490 and other references disclose that suitable water-absorbing and swellable hydrocolloid gums commonly include hydrocolloids such as sodium carboxymethylcellulose, pectin, gelatin, guar gum, locust bean gum, gum karaya, and mixtures thereof. The elastomers used in the continuous phase commonly include polyisobutylenes with which additives such as butyl rubber may be blended. The references also disclose that the elastomeric phase may contain a styrene block copolymer component to help provide extensibility and recoverability from modular strains to the composition. In addition, such skin barrier compositions may include mineral oil, to increase stretchability and adhesiveness of the blend, and suitable tackifying agents and antioxidants.

Skin barrier materials are not only used for ostomy care but also more generally for wound care. Such barrier materials may constitute the skin-contacting layers of relatively flat wafers or discs to be used as wound dressings or as the adhesive sealing rings for helping to secure ostomy pouches in place. Caulking rings and strips of relatively soft hydrocolloid materials such as karaya are commonly added to the skin barrier surfaces of planar faceplates to help ensure effective non-irritating seals directly about patients' stomas. Hydrocolloid-containing pastes are often used for a similar purpose, although such pastes are sometimes objectionable because of the irritation produced by their volatile solvents (usually alcohol).

The term "skin barrier" may also include the class of pliant, skinfriendly, moisture-absorbent materials commonly referred to as hydrogels. Hydrogels are known that also have adhesive characteristics, and such adherent hydrogels are also believed suitable for use in fabricating the skin barrier strips of this invention.

The present invention takes the form of an elongate rectilinear strip of skin barrier material that may be cut to desired length and formed, stretched and/or molded by a user into a generally circular shape or into some other shape that extends about and follows the outline of a wound or stoma. Alternatively, smaller portions of the strip may be torn or cut away and molded between the fingers for insertion into spaces between skin folds and other surface irregularities where fluid leakage might otherwise occur. In a preferred embodiment, the strip may be formed of a pliant skin barrier material that is non-flowable, so that when the strip is formed into a ring it may serve at least to a limited extent as a convex pressure ring about a stoma or wound.

A characterizing feature is that the strip is of generally triangular cross section and, more specifically, has the cross section of a triangle with at least two, and preferably three, unequal sides. A user desiring to form such strip into a ring to be interposed between the skin and the surface of a wound dressing or ostomy faceplate therefore has the option of forming rings of at least two, and preferably three, different levels of projection depending on which of the strip's side surfaces is coplanar with, and sealed to, the barrier surface of the dressing or faceplate.

DRAWINGS

FIG. 1 is a perspective view of a barrier strip embodying this invention.

FIG. 2 is a cross sectional view of the strip.

FIG. 3 is a plan view showing the strip formed into a ring and applied to the skin barrier surface of an ostomy faceplate.

FIG. 4 is a cross sectional view taken along line 4—4 of FIG. 3.

FIG. 5 is a cross sectional view similar to FIG. 4 but showing the strip formed into a ring providing a greater extent of projection.

FIG. 6 is a cross sectional view of a strip constituting a second embodiment of the invention.

FIG. 7 is a cross sectional view of a strip constituting a third embodiment of the invention.

DETAILED DESCRIPTION

In FIGS. 1–5, the numeral 10 designates an elongate strip of skin barrier material. As shown most clearly in FIG. 2, the strip is of generally triangular cross section with at least two sides of the triangle being of unequal length. In the preferred embodiment shown, all three sides 11, 12, and 13 are of different lengths resulting in a scalene triangular shape. Each of the sides of the strip may be flat or planar, with such sides meeting along relatively sharp corners or edges, but in a preferred embodiment it is believed desireable that the corners be rounded as shown. Furthermore, while they as shown in the drawings to be flat or planar, one or more of such sides may be slightly concave or convex. For example, side 12 may be concave, as represented by phantom line 12a in FIG. 2 or, alternatively, such side may be convex as indicated in the same figure by line 12b. In some cases it may be desireable to make one or more of the sides with portions that are alternately concave and convex, when viewed in section, as indicated by phantom line 11a. All such variations should be relatively slight departures from true flatness so that the strip in any case is substantially triangular in cross section.

FIG. 3 shows the strip 10 formed into a ring or closed loop and applied to the adhesive surface of a conventional ostomy wafer or faceplate 14. Such a faceplate has an adhesive layer 15 of conventional skin barrier material and a backing layer 16 formed of a flexible film or fabric, all as well known in the art. The faceplate also has an opening 17 that may be shaped and sized to match a patient's stoma 18. The ring or loop formed by strip 10 also defines an opening of similar size and shape as that of the faceplate. One side 12 of the ring is in direct adhesive contact with the adhesive surface of barrier layer 15.

FIG. 4 shows the strip 10 oriented in one of three possible positions to produce a selected extent of axial projection or protrusion. Where a greater extent of projection is desired, the strip may instead be oriented as depicted in FIG. 5 with the shortest side 13 in adhesive contact with the generally planar barrier layer 15. The extent of projection may thus be controlled by the user to meet the requirements for different patients depending, for example, on the extent of annular pressure that needs to be applied to cause a stoma, such as a recessed stoma, to extend into a collection pouch to which the faceplate is attached.

Most advantageously, the cross sectional shape is that of that of triangle that is both scalene and oblique, meaning that none of the corners is a right angle and all three sides are of unequal length. Analyzed in the same way, strip 10' shown in FIG. 6 also has unequal sides 11', 12', and 13'; however the corners were sharp, the cross sectional triangular shape is that of a right scalene triangle. Like the embodiment of FIG. 2, the embodiment of FIG. 6 may be formed and positioned to produce closed loops or rings having any of three different levels of projection.

FIG. 7 illustrates a third embodiment of the invention in which strip 10" is also of triangular cross sectional configuration but two of its sides 11" and 12" are of equal length, and are longer than the third side 13", resulting in a cross sectional configuration that is generally that of an isosceles triangle. Since strip 10" can be formed and adjusted to produce closed loops of only two different levels of axial extension or projection, the third embodiment is somewhat less advantageous than the first or second embodiments.

The barrier material from which strips 10, 10', and 10" are formed may be any of a variety of known skin barrier compositions. Depending on the selection of ingredients and their proportions, the properties of softness, tackiness, fluid absorbency, extensibility and recoverability, may be varied considerably for different applications. One skin barrier formulation that is believed to be particularly suitable is disclosed in U.S. Pat. No. 5,492,943 and is commercially available under the designation "Flextend" from Hollister Incorporated, Libertyville, Ill., but other skin barrier compositions having different properties, including adhesive hydrogels, may be selected.

What is claimed is:

1. An elongate and rectilinear strip of sticky, pliant, stretchable, moisture-absorbing and skinfriendly skin barrier material having both wet and dry tack, said strip being of a general uniform cross section throughout its length; said cross section being generally that of a triangle having at least two unequal sides.

2. The strip of claim 1 in which said cross section is that of a scalene triangle.

3. The strip of claim 1 in which said cross section is that of an oblique scalene triangle.

4. The strip of claim 2 in which said cross section is that of a right scalene triangle.

5. The strip of claim 1 in which said cross section is that of an isosceles triangle.

6. The strip of claim 1 in which said strip has at least one rounded corner when viewed in cross section.

7. The strip of claims 1, 2, 3, 4, 5 or 6 in which at least one of said sides is flat.

8. The strip of claims 1, 2, 3, 4, 5 or 6 in which at least one of said sides is concave when said strip is viewed in cross section.

9. The strip of claims 1, 2, 3, 4, 5 or 6 in which at least one of said sides is convex when said strip is viewed in cross section.

10. The strip of claims 1, 2, 3, 4, 5 or 6 in which at least one of said sides has portions that are alternately concave and convex when said strip is viewed in cross section.

11. The strip of claim 1 in which said skin barrier material has a continuous phase of an elastomeric adhesive in which a discontinuous phase of hydrocolloid particles is dispersed.

12. The strip of claim 1 in which said skin barrier material is an adhesive hydrogel.

13. A method of using an elongate and rectilinear strip of sticky, pliant, stretchable, moisture-absorbing skin barrier material having generally uniform cross section throughout its length with said cross section being generally that of a triangle having at least two unequal sides, comprising the steps of orienting said strip so that it will project a selected distance from a skin or wound surface when one of said sides is adhered to said surface, and thereafter adhering a wafer having a layer of adhesive skin barrier material to said surface, with said oriented triangular strip interposed between said surface and said skin barrier layer of said wafer.

14. The method of claim 13 in which said skin barrier material of said strip has a continuous phase of an elastomeric adhesive in which a discontinuous phase of hydrocolloid particles is dispersed.

15. The method of claim 13 in which said skin barrier material of said strip is an adhesive hydrogel.

16. The method of claims 13, 14 or 15 in which said cross section of said strip is that of a scalene triangle.

17. The method of claims 13, 14 or 15 in which said cross section of said strip is that of an oblique scalene triangle.

18. The method of claims 13, 14 or 15 in which said cross section of said strip is that of an isosceles triangle.

* * * * *